United States Patent
Kimchi (12)

(10) Patent No.: US 6,255,293 B1
(45) Date of Patent: Jul. 3, 2001

(54) PREVENTION OF METASTASIS WITH 5-AZA-2'-DEOXYCYTIDINE

(75) Inventor: Adi Kimchi, Raanana (IL)

(73) Assignee: Yeda Research and Development Co., Ltd., Rehovot (IL)

( * ) Notice: Subject to any disclaimer, the term of this patent is extended or adjusted under 35 U.S.C. 154(b) by 0 days.

(21) Appl. No.: 09/359,915

(22) Filed: Jul. 26, 1999

Related U.S. Application Data

(63) Continuation-in-part of application No. 09/121,988, filed on Jul. 24, 1998, now abandoned.

(51) Int. Cl.[7] .............................. A61K 31/70; C12Q 1/68; C12Q 1/70; G01N 33/53
(52) U.S. Cl. .................................... 514/49; 435/5; 435/6; 435/7.1
(58) Field of Search ................................ 435/6, 7.1, 91.2, 435/5; 514/49

(56) References Cited

FOREIGN PATENT DOCUMENTS

| 9510630 | 4/1995 | (WO) . |
| 9839429 | 9/1998 | (WO) . |

OTHER PUBLICATIONS

Inbal et al., "DAP kinase links the control of apoptosis to metastasis", *Nature*, vol. 390, pp. 180–184, (1997).

Kissil et al., "DAP–kinese loss of expression in various carcinoma and B–cell lymphoma cell lines: possible implications for role as tumor suppressor gene", *Oncogene*, vol. 15, pp. 403–407, (1997).

Gonzalgo et al., "Low Frequency of p16/CDKN2A Methylation in Sporadic Melanoma: Comparative Approached for Methylation Analysis of Primary Tumors", *Cancer Research*, vol. 57, pp. 5336–5347, (1997).

Katzenellenbogen et al., "Hypermethylation of the DAP–Kinase CpG Island is a Common Alteration in B–cell Malignancies", *Blood*, vol. 93, No. 12, (1999).

Herman et al., Methylation–specific PCR: A novel PCR assay for methylation status of CpG island *Proc. Natl. Acad. Sci.*, vol. 93, pp. 9821–9826, (1996).

*Primary Examiner*—Robert A. Schwartzman
(74) *Attorney, Agent, or Firm*—Browdy & Neimark

(57) ABSTRACT

Tumor metastases are often caused by the elimination of the tumor suppressive effect of DAP-kinase. If the lack of DAP-kinase activity is due to methylation of the DAP-kinase gene, then the tumor suppressive activity of DAP-kinase can be restored by treating with a demethylating agent such as 5-aza-2'-deoxycytidine. Thus, tumor cells of a patient are screened to determine whether DAP-kinase protein is produced by the cells and, if not, to determine if the cells contain DAP-kinase genes which are methylated. If the latter case is so, then the patient is treated with a demethylating agent such as 5-aza-2'-deoxycytidine. If the cells produce DAP-kinase protein, the patient may be prophylactically treated with a demethylating agent or a DNA methyltransferase inhibitor, such as 5-aza-2'-deoxycytidine, in order to prevent eventual loss of DAP-kinase by methylation of the gene and therefore prevent eventual metastasis.

7 Claims, 3 Drawing Sheets

—△— NO TREATMENT
—□— PBS, DAY 1
—■— 5-aza-dC, DAY 1
—◇— PBS, DAY 30
—◆— 5-aza-dC, DAY 30
—○— PBS, DAY 50
—●— 5-aza-dC, DAY 50

PREVENTION OF METASTASIS WITH 5-AZA-2'-DEOXYCYTIDINE

CROSS-REFERENCE TO RELATED APPLICATIONS

The present application is a continuation-in-part of U.S. application Ser. No. 09/121,988, filed Jul. 24, 1998, abandoned.

FIELD OF THE INVENTION

The present invention relates to methods for screening cancer patients for susceptibility to a particular treatment protocol and to a method of treatment of those patients found positive in the screen, and more particularly to such screens and methods based on screening for DAP-kinase methylation and treatment with 5-aza-2'-deoxycytidine.

BACKGROUND OF THE INVENTION

Loss or inactivation of tumor suppressor genes is among the genetic defects which participate in the multi-step process which causes cancer. Some of the tumor suppressor genes are part of the genetic machinery which controls programmed cell death, also named apoptosis, and therefore their deregulation severely disrupts the normal tissue homeostasis terminating in tumor growth. Various types of genetic and epigenetic deregulations can inactivate tumor suppressor genes including DNA deletions, mutations, translocations, chromosomal losses and DNA methylations.

DAP-kinase is a positive mediator of apoptosis, recently identified as a tumor suppressor gene (Deiss et al., 1995; Cohen et al., 1997; Kissil et al., 1997; Inbal et al., 1997; Cohen et al., 1999). This calcium/calmodulin-dependent serine/threonine kinase mediates cell death triggered by various signals including different cytokines, detachment from extracellular matrix and oncogenes. Several independent research lines suggested that DAP-kinase is a potential tumor suppressor gene:

1. DAP-kinase gene expression was found to be lost at high frequency in human tumor cell lines. Both the mRNA and protein expression levels were found below detection limits in 70% of B-cell lymphoma and leukemia cell lines and in 30% of cell lines derived from bladder carcinomas, breast carcinomas, and renal cell carcinomas (Kissil et al., 1997). This stood in sharp contrast to the finding that DAP-kinase mRNA was widely expressed in all the tested human and murine tissues, as well as in many immortalized cell lines established from normal cells. In two bladder carcinoma and in one of the B cell lymphoma cell lines, DAP-kinase expression could be restored by treatment of cells with 5-aza-2'-deoxycytidine, a drug which inhibits DNA methylation (Kissil, et al., 1997). This suggested that loss of expression in these particular cases was due to DNA methylation, as previously reported for other tumor suppressor genes, such as p16, VHL, and pRB. Yet, it was found, from the tumor cell lines screen, that demethylation is not an exclusive mechanism for suppressing DAP-kinase expression, in accordance with the well established paradigm that tumor suppressor genes may be lost or inactivated by multiple genetic or epigenetic alterations. These experiments provided the first hint that DAP-kinase inactivation may possibly be a causative factor in the formation of tumors, as was further tested in experimental animal model systems.

2. In parallel, a second approach was carried out that directly tested in animal models whether the DAP-kinase gene has tumor suppressor functions. In these experiments, the normal expression levels of DAP-kinase were restored into tumor cells that had lost it, and the impact of this genetic manipulation on the tumorigenic properties of the cells was assayed. It was found that high-metastatic lung carcinoma clones, originating from two independent murine lung tumors, lacked DAP-kinase expression, in contrast to their low-metastatic counterparts which expressed normal levels. Wild-type DAP-kinase was introduced into the high-metastatic Lewis carcinoma cells and stable transfected clones in which DAP-kinase expression was restored to physiological levels were isolated and assayed for their tumorigenic and metastatic activity in syngeneic mice. Strikingly, restoration of physiological levels of DAP-kinase into the high-metastatic Lewis carcinoma cells suppressed their ability to form lung metastases after intravenous injections into mice. The in vivo effects were proportional to the levels of the ectopically expressed DAP-kinase. The transgene also delayed local tumor growth in a foreign micro environment, yet this feature was less sensitive to DAP-kinase ectopic expression than the metastatic activity. Once tumors appeared at the late time points, they were capable of generating spontaneous metastases in the lungs. Examination of these secondary lung lesions indicated that the tumor cells have lost expression from the DAP-kinase transgene. The loss was due to specific DNA methylation which suppressed expression, since treatment of the cells with 5-aza-2'-deoxycytidine in vitro, after their removal from the lung lesions, restored DAP-kinase expression to high levels (Inbal et al., 1997).

3. By selecting in vivo rare lung metastases, after injections of the original low-metastatic cells into irradiated syngeneic mice, it was found that the development of these metastatic lesions correlated with loss of the endogenous DAP kinase expression. Moreover, treatment of cells recovered from one of these DAP-kinase negative lung lesions with 5-aza-2'-deoxycytidine, restored protein expression to the normal levels (Inbal et al., 1997). DNA methylation was therefore also responsible for silencing the endogenous DAP-kinase gene in some of the in vivo selected lung lesions. Altogether, these experiments suggested that loss of DAP-kinase expression provides a positive selective advantage during the formation of lung metastases.

SUMMARY OF THE INVENTION

Accordingly, it is an object of the present invention to overcome the deficiencies of the prior art.

It is another object of the present invention to provide a screening procedure for determining whether a given cancer patient is most likely to be susceptible to treatment for the prevention of metastases using a DNA demethylating agent.

It is a further object of the present invention to provide such a screening method which first involves determining whether DAP-kinase protein is produced by the patient's tumor cells and, if not, determining if such cells contain DAP-kinase genes which are methylated.

It is still a further object of the present invention to provide a method of treatment to decrease the chance that tumor cells will metastasize.

It is still another object of the present invention to provide such a method of treatment which involves administering a DNA demethylating agent if the screening procedure shows that the patient is likely to be susceptible to such treatment.

These and other objects of the present invention are accomplished by means of the embodiments disclosed in the present specification and equivalent procedures. A specific embodiment of a screen which is in accordance with the present invention is a screening procedure to determine whether primary tumor cells or metastatic tumor cells lack DAP gene expression, and particularly DAP kinase expression. More particularly, such a screening procedure is to determine whether such cells which do not have DAP, and particularly DAP-kinase activity, display a methylated form of the DAP gene, and particularly of the DAP-kinase gene. Cells which are positive for such a screen are particularly good candidates for treatment by means of demethylation agents, such as 5-aza-2'-deoxycytidine, in order to demethylate the gene and restore DAP function, and particularly DAP-kinase function.

Further in accordance with the present invention is the therapeutic method of preventing or limiting the spread of metastases by treatment of a patient with a therapeutically effective amount of a demethylating agent, such as 5-aza-2'-deoxycytidine, so as to prevent methylation of the DAP genes, and particularly the DAP-kinase gene, or to demethylate genes which have lost their ability to express the DAP product due to methylation of the gene, thereby restoring the biological metastasis-preventing activity of the endogenous DAP genes, and particularly the DAP-kinase gene. This method of therapeutic treatment is particularly useful for the treatment of patients whose tumor cells have been shown to have a methylated DAP-kinase gene. It is further useful for the treatment of tumor cells which have high DAP-kinase expression levels in order to prevent eventual methylation thereof.

DESCRIPTION OF THE DRAWINGS

The present invention will be better understood from the following detailed description of preferred embodiments, taken in conjunction with the following drawings in which:

In FIG. 1A, intrafootpad (i.f.p.) injection of D122-pCDNA cells (clone 18-cont.) were made into C57BL/6 mice. Mice groups containing eight individuals each were either i.p. injected with 5-aza-2'-deoxycytidine at a 12.5 $\mu$M or 6.25 $\mu$M dose (half-filled and filled symbols, respectively), PBS (open symbols), or not injected at all (triangles). The i.p. injections were initiated at day one (squares) or day 30 (diamonds) after i.f.p. injections. Values are mean footpad diameter of a group. In FIGS. 1B and 1C, i.f.p. injections of D122 DAPk cells (clone 42-DAPk) were made into C57BL/6 mice. The same symbols as in FIG. 1A are used, including i.p. injections initiated at day 50 (circles). The two doses of 5-aza-2'-deoxycytidine used are depicted in different graphs. FIG. 1B shows the dose of 12.5 $\mu$M and FIG. 1C at 6.25 $\mu$M. Note that the symbols connected by a line correspond to the averaged footpad diameter of a group, while those that were not linked by a line correspond to individual apparent values, whose SD deviates above a certain threshold and thus were not included in the average calculations.

FIG. 2A shows the results with three tumor types and FIG. 2B shows the results with four other tumor types.

DETAILED DESCRIPTION OF THE INVENTION

Figure 1A:
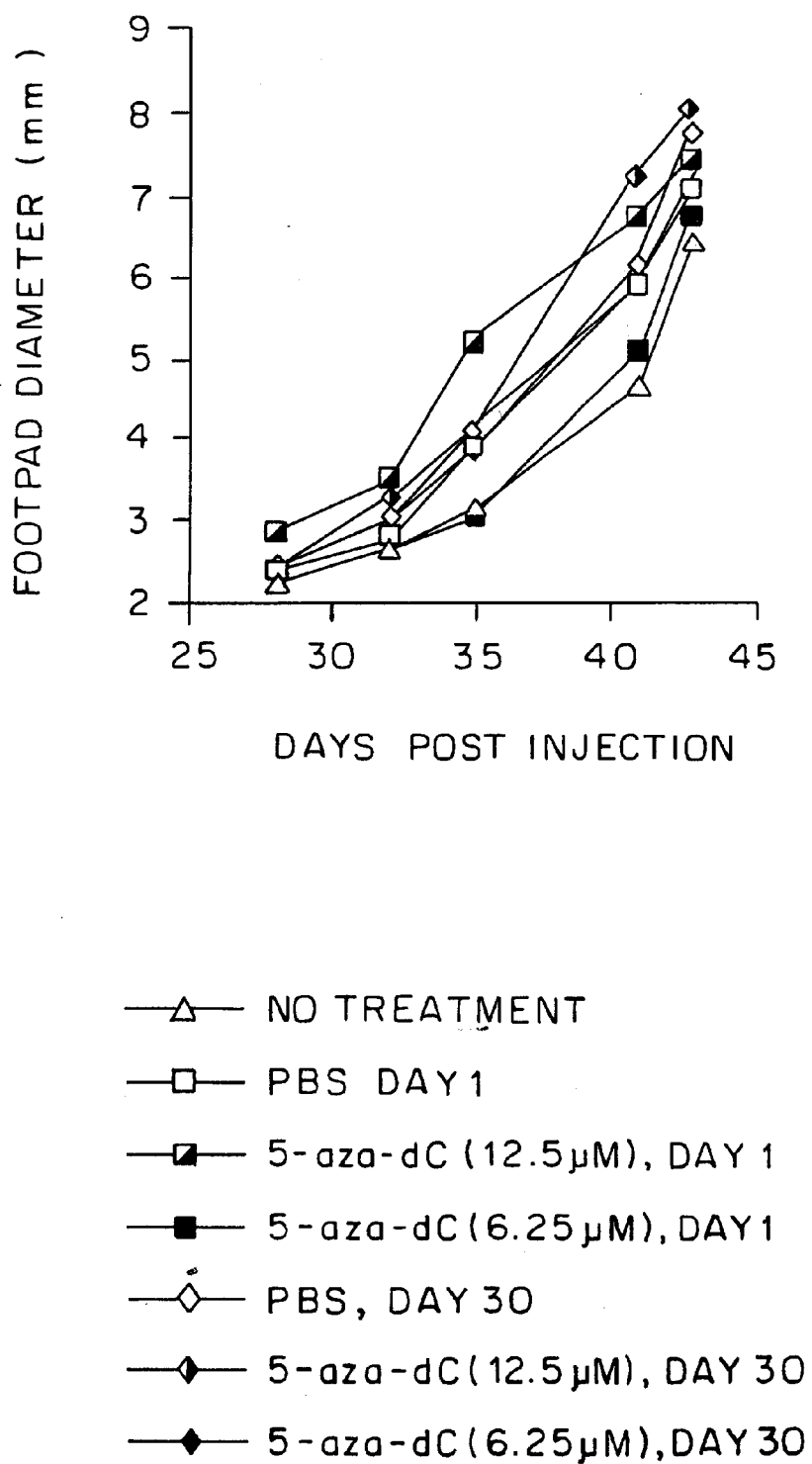
FIGS. 1A–C show the delayed formation of local tumors in mice injected with D122-DAPk cells and treated with 5-aza-2'deoxycytidine.

The present invention is based on the finding that the DAP-kinase gene is a target for DNA methylation, and that tumor cells frequently use this mechanism to eliminate or reduce DAP-kinase expression and by that means to increase their tumorgenicity. Therefore, patients carrying tumor cells that are still DAP-kinase positive cells may be treated with a demethylating agent such as the 5-aza-2'-deoxycytidine drug, which is a potent inhibitor of DNA methylation, to prevent methylation of DAP-kinase gene and thereby help to prevent metastases. The second group of tumors to be treated with 5-aza-2'-deoxycytidine will be those comprising of DAP-kinase negative cells that, in the screening tests, are shown to possess methylations which prevent expression. Treatment of this group of tumors with a demethylating agent will help to reduce their metastatic potential. In this respect it should be pointed out that DNA methylation is not an exclusive mechanism to eliminate DAP-kinase. Other ways consist of genomic rearrangements or deletions within the gene which obviously should be resistant to the 5-aza-2'-deoxycytidine drug treatments. Upon recognition of the specific DAP-kinase DNA sequences which are targets for methylation, it will be possible to score individual tumors and choose those which display the specific methylation. A PCR-based method for identifying the methylation status of potential DNA sites in freshly isolated tumor specimens was recently described and adapted to our initial tumor screen from cancer patients (see detailed description of the invention). Its advantage is that it can be applied in DNA samples isolated directly from the patient's tumor, and that the assay is relatively simple and rapid.

The primary goal of this concept is to treat with 5-aza-2'-deoxycytidine cancer patients who carry tumors which are DAP-kinase negative due to DNA methylation. The inventive procedure is to combine a method for screening of tumor cells together with a protocol of patient treatment which will consist of routine injections with the 5-aza-2'-deoxycytidine drug. The screening test will select the patients who will be chosen for further treatment. The patients carrying tumors with methylated DAP-kinase gene will be chosen in attempts to attenuate tumor growth and reduce metastasis.

Another option will be to include in the chosen group patients whose primary tumors are still DAP-kinase positive, to prevent further DNA methylation especially during the critical period after the surgery in which secondary metastases may appear.

Protocols of 5-aza-2'-deoxycytidine treatment of patients were approved in the past and further used in the USA for other purposes, such as for use as an anticancer drug which induces cellular differentiation and enhanced expression of genes involved in tumor suppression, immunogenicity and programmed cell death. It has been recognized that administration of this compound blocks DNA methylation. See, for example, Thibault et al, (1998), Momparler et al, (1997), Schwartsmann et al, (1997), Willemze et al, (1997) and Momparler, (1997). However, the use of this drug specifically to prevent or reverse methylation of the DAP-kinase gene in cancer patients had never been suggested prior to the present invention.

Thus, the present invention contemplates, prior to administration of this drug, screening patients to find those whose tumors are most likely to be susceptible to treatment by this drug. This is accomplished in accordance with the present invention by first screening for DAP-kinase protein production by means of any appropriate assay. A preferred assay is an immunoassay using a labeled monoclonal antibody against the DAP-kinase protein. Thus, a simple immunostaining assay will show the presence or absence of DAP-kinase products in biopsy of the tumor cells. Any other immunoassay or assay for the presence of the protein or mRNA which encodes this protein may be used as long as it will result in a determination of whether or not the DAP-kinase protein is being expressed by the tumor cells. The existence of such assays and the performance of such assays is well within the knowledge and skill of those of ordinary skill in this art.

If the DAP-kinase protein is being abundantly produced, particularly if the tumor cells are the cells of a primary tumor, then the patient from whom such cells were taken is a candidate for treatment with a demethylating agent such as 5-aza-2'-deoxycytidine (also known as decitabine), in order to prevent methylation of the gene and maintain the tumor suppressive and metastasis suppressive effects of the DAP-kinase protein.

If the initial screen is negative, showing that there is no production or very little production of the DAP-kinase protein, this will not establish whether or not the patient is a candidate for treatment with a demethylating agent such as 5-aza-2'-deoxycytidine. There are many reasons why cells may not be producing the DAP-kinase protein, including rearrangement or mutation of the gene sequence. In order to establish that such cells are candidates for treatment with a demethylating agent, it should first be determined that the cells possess the DAP-kinase gene but that the DAP-kinase gene is being prevented from expression because of methylation. This can be accomplished by means of the known technique of Herman et al. (1996), the entire contents of which are hereby incorporated herein by reference. In this technique, the DNA from cells is treated with sodium bisulfate, which converts cytosines in the DNA to uracils except when the cytosine is methylated. By using appropriate DNA primers, one can conduct PCR in such a manner as to distinguish DNA which contains cytosine at the methylation site, thereby establishing that the DNA must have been methylated, from DNA which contains uracil at the methylation site, thereby establishing that the DNA is not methylated. Methylation sites in the 5'-UTR region of DAP-kinase have been recently identified (Katzenellenbogen et al., 1999) and the DNA primers were designed to determine whether the gene is methylated at those sites. The method was recently utilized by the inventor in a first screen of patient's tumors (see the detailed description, infra). If the cells which were negative in the DAP-kinase protein immunoassay are positive in the PCR assay for methylation, then such a patient is an excellent candidate for treatment by a demethylating agent such as 5-aza-2'-deoxycytidine. This drug would be expected to demethylate the DAP-kinase gene and permit it to once again express its DAP-kinase protein which has a tumor suppressive and metastasis preventative effect. This effect has been shown in a mouse model in the experiments set forth hereinbelow.

The 5-aza-2'-deoxycytidine may be administered in manners known to those of ordinary skill in the art in view of the existing published clinical trials of this drug as an anticancer medication. Preferably, the administration is intravenous and is continued on a daily basis until the effect is shown. Clinicians of ordinary skill in the art can readily determine appropriate dosages and means of administration in light of the knowledge of the skill in the art and empirical results obtained in the course of treatment.

It is contemplated that the administration of 5-aza-2'-deoxycytidine or any other demethylating agent be preferably in conjunction with other chemotherapy. It may also be preferably used shortly after surgery when risk of metastasis is the greatest.

While the only agent for causing demethylation of methylated DNA or for preventing methylation of DNA which is used in the present examples is 5-aza-2'-deoxycytidine, those of ordinary skill in the art will understand that any other agent which accomplishes these functions can also be used in the present invention. For example, other compounds which have been reported in the literature to inhibit DNA methylation include 5,6-dihydro-5-azacytidine, 5-azacytidine, and 1-β-D-arabinofuranosyl-5-azacytidine. See Antonsson et al. (1987), Covey et al. (1986), and Kees et al. (1995). Any compound known to be a cytosine specific DNA methyltransferase inhibitor would be expected to be operable in the present invention. Any such compound can be readily tested without undue experimentation in order to determine whether or not it works in the context of the present invention in the same manner as 5-aza-2'-deoxycytidine, for example by repeating the experiments of the present examples with each proposed demethylating agent.

The present invention will now be further explained by means of the following non-limiting examples.

EXAMPLE 1

Mouse Model System

One of the most important experiments for testing the feasibility of the concept was to perform in vivo treatment of mice with 5-aza-2'-deoxycytidine in tumorigenicity assays which are DAP-kinase dependent. A success in a mouse model system is critical for the proposed invention. For that purpose the mice were injected with the DAP-kinase transfectants of the mouse carcinoma lung cells (D122-DAP-kinase—clone 42-DAPk). This is one of the transfectants in which high levels of DAP-kinase delayed local tumor growth; yet, specific DNA methylation suppressed expression from the transgene and restored their aggressiveness. As a control we used D122 transfected with an empty vector (18-DAPk). This clone is null for DAP-kinase and in vitro treatment with 5-aza-2'-deoxycytidine had no effects on DAP-kinase expression.

Figure 1B:
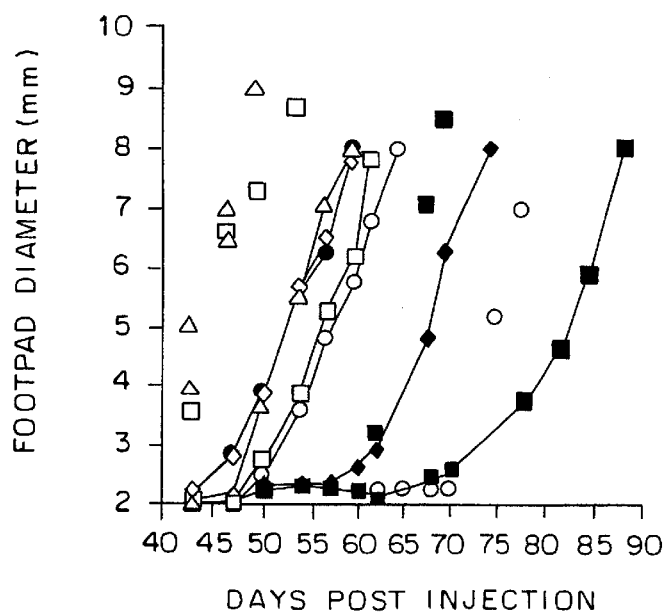
Figure 1C:
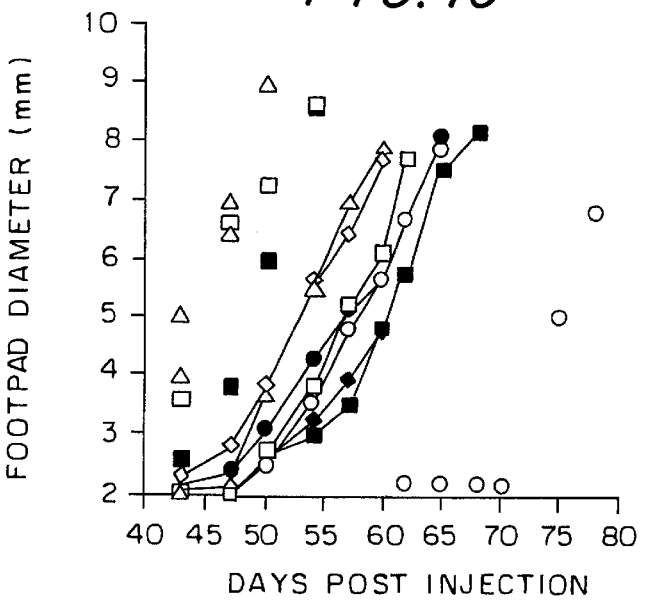

The two different D122 clones were injected into the foot pads of C57BL/6 mice using the protocol which was described in detail in Inbal et al, (1997), the entire contents of which are hereby incorporated herein by reference. These mice were then i.p. injected with 5-aza-2'-deoxycytidine at two doses. The injections were performed twice a week, beginning either at day 1, or day 30 (for both clones), or also at day 50 (for clone 42-DAPk). The control 18-DAPk clone formed local tumors appearing at day 30, and those were not influenced at all by the 5-aza-2'-deoxycytidine injections (FIG. 1A). This provided a perfect background for the experiments since it proved that other genes besides DAP kinase were not involved in this model system. In all mice groups injected with clone 42-DAPk the tumors started to appear at day 45 as previously reported (Inbal et al. (1997)). Here, the effect of the 5-aza-2'-deoxycytidine drug was prominent. The injections with 12.5 μM drug concentrations delayed tumor growth very significantly (FIG. 1B). The effect was maximal when injections begun at day 1. It was still significant when injections were initiated at day 30, and no effects were achieved at day 50 (FIG. 1B). The lower dosage of the 5-aza-2'-deoxycytidine (6.25 μM) was not effective (FIG. 1C).

These lines of experiments prove that it is possible to suppress local tumor outgrowth by continuous 5-aza-2'-deoxycytidine drug injections. The sustained drug levels in circulation prevent DAP-kinase methylation and thus keep high DAP-kinase expression levels and delay tumor growth. No side effects were monitored, and tumors which are null for DAP-kinase are not affected by the drug.

EXAMPLE 2
The Screening Test for Methylation of DAP-Kinase Gene in Primary Human Malignancies The tumor collection in the laboratory of the present inventors consists of 30 specimens of solid carcinomas (colon, breast, and a few others; see Table 1) which were frozen in liquid nitrogen immediately after the patient's operation. In each case a sample of normal tissue which surrounds the tumor was removed and frozen in parallel. Patients' carcinoma specimens were screened with the intention of: 1. Finding out whether DNA methylations of DAP-kinase take place during cancer development as one of the validation tests for linking DAP-kinase to human cancer. 2. Providing an easy method for screening tumor cells for DAP-kinase methylation status as a prognostic test which predicts the metastatic potential of the tumor. 3. To couple the screening method to a protocol of patient treatment which will consist of routine injections with the 5-aza-2'-deoxycytidine drug.

For the screen of tumor DNA for DAP-kinase methylations, the Methylation Specific PCR (MSP) technique was used which was developed by Katzenellenbogen et al. (1999), the entire contents of which are hereby incorporated herein by reference. This PCR method detects methylations of CpG sites in CpG islands. It can be used on small amounts of DNA which can be even extracted from paraffin-embedded samples. It is based on chemical modification of cytosine to uracil by sodium bisulfide treatment. In these reactions all cytosines are converted to uracil, but those that are methylated are resistant to this modification and remain as cytosine. Primers specific for either methylated or the modified unmethylated DNA are then used for DNA amplifications. The specific primers used in this experiment were the same as those reported in Katzenellenbogen et al. (1999). Methylation in CpG sites is scored by gel fractionations of the amplified DNA and detecting positive signals with the corresponding primers. The primer sequences for DAP-kinase were derived from the 5' region of the gene which contains a typical GpC island.

More specifically, the specific methylation-specific polymerase chain reaction (MSP) technique which was used was as follows: DNA methylation patterns in the CpG island of DAP-kinase were determined by chemical treatment with sodium bisulfite and subsequent use of the previously described polymerase chain reaction (PCR) procedure (Herman et al., (1996)). MSP distinguishes the methylation status of a given region based on sequence changes produced by sodium bisulfite treatment (Herman et al., (1996)) and has been previously validated for genes, including p16 (Herman et al., (1996); Gonzalgo et al., (1997), p15, E-cadherin, VHL (Herman et al. (1996)), hMLH1 (Herman et al. (1998), the estrogen receptor (Lapidus et al. (1998)), GSTπ (Esteller et al. (1998)), and MGMT (Esteller et al. (1999)), and for the diagnosis of the imprinting disorder of Prader-Willi and Angelman's syndromes (Kubota et al. (1997), Zeschnigk et al. (1997), Jacobsen et al. (1998), and Huerta Rivas et al. (1998)). The primer sequences designed for DAP-kinase spanned 6 CpGs in total within the 5' region of the gene. Primer sequences for unmethylated reaction were 5'-GGA GGA TAG TTG GAT TGA GTT AAT GTT-3' (SEQ ID NO:1) (sense) and 5'-CAA ATC CCT CCC AAA CAC CAA-3' (SEQ ID NO:2) (antisense). Primer sequences for methylated reaction were 5'-GGA TAG TCG GAT CGA GTT AAC GTC-3' (SEQ ID NO:3) (sense) and 5'-CCC TCC CAA ACG CCG A-3' (SEQ ID NO:4) (antisense). The 5' position of the sense unmethylated and methylated primers corresponds to bp 2 and 5 of Genbank sequence no. X76104, respectively. Both antisense primers originate from bp 87 of this sequence. The annealing temperature for both the unmethylated and methylated reactions was 60° C. All MSP reactions were performed with positive and negative controls for both unmethylated and methylated alleles and a no DNA control.

Figure 2A:
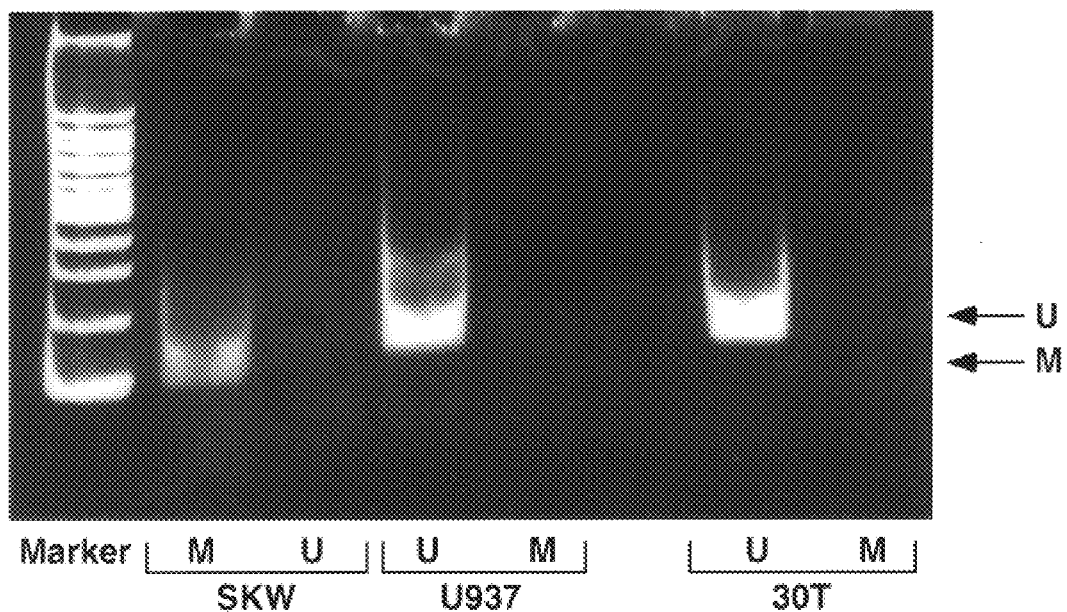
FIGS. 2A and B show the result of Methylation Specific PCR (MSP) analysis.
Figure 2B:
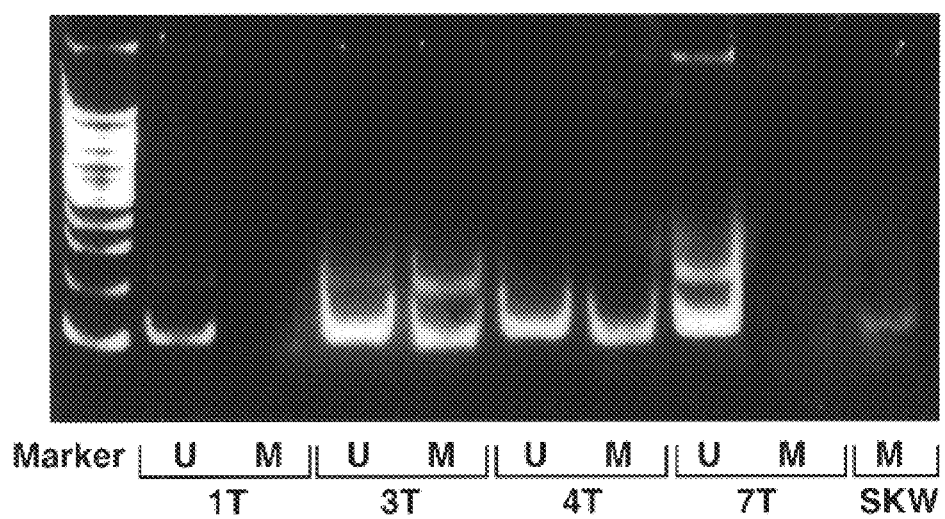

In the first step, the specificity of the reactions was tested. The SKW B cell lymphoma cell line was used, which does not express DAP-kinase due to DNA methylations (Kissil et al., 1997). The MSP analysis showed that only methylated copies (M) of the DAP gene could be detected in these cells (FIG. 2A). In contrast, U937 cells which express DAP-kinase has only unmethylated copies (U) of DAP-kinase gene (FIG. 2A). All the normal tissues screened to date had only unmethylated copies. The tumors were then analyzed. Methylation of DAP-kinase CpG island in 26% of tested cases (total cases 8/31–26%; colon cancer 6/28–21%; breast 2/3–66%; see Table 1 for details) was observed. FIGS. 2A and 2B illustrate a few examples. It shows that tumors #30 and #7 are completely negative for methylations while tumors #3 and #4, are positive. Tumor #1 showed traces of DNA methylation (below 0.1%) and therefore scored in Table 1 as negative. All the tumors scored as positive in this assay showed a mixture of methylated and unmethylated copies of DAP-kinase representing either methylation of the island on one of the alleles or possible contamination of the tested sample with normal cells present in tumors (e.g., blood vessels, infiltrating white blood cells).

TABLE 1
Examination of DAP-kinase DNA methylations in patient's tumors

| Serial # | Type | MSP |
| --- | --- | --- |
| 1 | colon | (−) |
| 2 | colon | (−) |
| 3 | breast | (+) |
| 4 | breast | (+) |
| 5 | colon | (−) |
| 6 | colon | (−) |
| 7 | colon | (−) |
| 8 | esoph. | (−) |
| 9 | colon | (+) |
| 10 | colon | (+) |
| 11 | colon | (−) |
| 12 | colon | (+) |
| 13 | colon | (−) |
| 14 | colon | (+) |
| 15 | colon | (−) |
| 16 | colon | (−) |
| 17 | breast | (−) |
| 18 | colon | (−) |
| 19 | colon | (−) |
| 20 | rhabdo. | (−) |
| 21 | colon | (−) |
| 22 | n/a | |
| 23 | n/a | |
| 24 | n/a | |
| 25 | colon | (−) |
| 26 | colon | (−) |
| 27 | n/a | |
| 28 | liver | (−) |
| 29 | colon | (−) |
| 30 | colon | (−) |
| 31 | colon | (+) |
| 32 | colon | (−) |
| 33 | colon | (−) |
| 34 | colon | (−) |
| 35 | colon | (+) |

The foregoing description of the specific embodiments o fully reveal the general nature of the invention that can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention. Thus the expressions "means to . . . " and "means for . . . ", or any method step language, as may be found in the specification above and/or in the claims below, followed by a functional statement, are intended to define and cover whatever structural, physical, chemical or electrical element or structure, or whatever method step, which may now or in the future exist which carries out the recited function, whether or not precisely equivalent to the embodiment or embodiments disclosed in the specification above, i.e., other means or steps for carrying out the same function can be used; and it is intended that such expressions be given their broadest interpretation.

REFERENCES

Antonsson et al., "Effect of 5-azacytidine and congeners on DNA methylation and expression of deoxycytidine kinase in the human lymphoid cell lines CCRF/CEM/o and CCRF/CEM/dCk-1", *Cancer Res.*, 47(14):3672–8 (1987).

Cohen et al., "DAP-kinase is a $Ca^{2+}$/calmodulin-dependent, cytoskeletal-associated protein kinase, with cell death-inducing functions that depend on its catalytic activity", *EMBO Journal*, 16(5):998–1008 (1997).

Cohen et al., "DAP-kinase participates in TNF-alpha- and Fas-induced apoptosis and its function requires the death domain", *J. Cell Biol.*, 146(1):141–148 (1999).

Covey et al., "Differences in DNA damage produced by incorporation of 5-aza-2'-deoxycytidine or 5,6-dihydro-5-azacytidine into DNA of mammalian cells", *Cancer Res.*, 46(11):5511–7 (1986).

Deiss et al., "Identification of a novel serine/threonine kinase and a novel 15-kD protein as potential mediators of the gamma interferon-induced cell death", *Genes Dev.*, 9(1):15–30 (1995).

Esteller et al., "Inactivation of glutathione S-transferase P1 gene by promoter hypermethylation in human neoplasia", *Cancer Res.*, 58:4515 (1998).

Esteller et al., "Inactivation of the DNA repair gene $O^6$-Methylguanine-DNA methyltransferase by promoter hypermethylation is a common event in human neoplasia", *Cancer Res.*, 59:793 (1999).

Gonzalgo et al., "Low frequency of p16/CDKN2A methylation in sporadic melanoma: Comparative approaches for methylation analysis of primary tumors", *Cancer Res.*, 57:5336 (1997).

Herman et al., "Methylation-specific PCR: A novel PCR assay for methylation status of CpG islands", *PNAS*, 93:9821–6 (1996).

Herman et al., "Incidence and functional consequences of hMLH1 promoter hypermethylation in colorectal carcinoma", *Proc. Natl. Acad. Sci. USA*, 95:6870 (1998).

Huerta Rivas et al., "Quick diagnosis of Prader-Willi and Angelman syndromes by means of methylation test by PCR", *An. Esp. Pediatr.*, 48:583 (1998).

Inbal et al., "DAP-kinase links the control of apoptosis to metastasis", *Nature*, 390:180–184 (1997).

Jacobsen et al., "Molecular screening for proximal 15q abnormalities in a mentally retarded population", *J. Med. Genet.*, 35:534 (1998).

Katzenellenbogen et al., "Hypermethylation of the DAP-kinase CgP island is a common alteration in B-cell malignancies", *Blood*, 93:4347–53 (1999).

Kees et al., "Biochemical pharmacology and DNA methylation studies of arabinosyl 5-azacytidine and 5,6-dihydro-5-azacytidine in two human leukemia cell lines PER-145 and PER-163", *Anticancer Drugs*, 6(2):303–10 (1995).

Kissil et al., "DAP-kinase loss of expression in various carcinoma and B-cell lymphoma cell lines: Possible implications for role as tumor suppressor gene", *Oncogene*, 15:403–407 (1997).

Kubota et al., "Methylation-specific PCR simplifies imprinting analysis", *Nat. Genet.*, 16:16 (1997).

Lapidus et al., "Mapping of ER gene CpG island methylation-specific polymerase chain reaction", *Cancer Res.*, 58:2515 (1998).

Momparler et al., "Pilot phase I–II study of 5-aza-2'-deoxycytidine (Decitabine) in patients with metastatic lung cancer", *Anticancer Drugs*, 8:358–368 (1997).

Momparler et al., "Pharmacological approach for optimization of the dose schedule of 5-Aza-2'-deoxycytidine (Decitabine) for the therapy of leukemia", *Leukemia*, 11 Suppl. 1:S1–6 (1997).

Schwartsmann et al., "Decitabine (5-Aza-2'-deoxycytidine; DAC) plus daunorubicin as a first line treatment in patients with acute myeloid leukemia: preliminary observations", *Leukemia*, 11 Suppl. 1:S28–31 (1997).

Thibault et al., "A phase II study of 5-aza-2'-deoxycytidine (decitabine) in hormone independent metastatic (D2) prostate cancer", *Tumori*, 84(1):87–9 (1998).

Willemze et al., "A randomized phase II study on the effects of 5-Aza-2'-deoxycytidine combined with either amsacrine or idarubicin in patients with relapsed acute leukemia: an EORTC Leukemia Cooperative Group phase II study (06893)", *Leukemia*, 11 Suppl. 1:S24–7 (1997).

Zeschnigk et al., "A single-tube PCR test for the diagnosis of Angelman and Prader-Willi syndrome based on allelic methylation differences at the SNRPN locus", *Eur. J. Hum. Genet.*, 5:94 (1997).

What is claimed is:

1. A method of screening tumor cells of a patient to determine those most likely to be susceptible to treatment for prevention of metastasis, comprising:
   a) determining whether DAP-kinase proteins are produced by said cells; and
   b) if the determining step of a) is negative, determining if said cells contain DAP-kinase genes which are methylated,
      whereby a positive outcome of the determining step b) indicates the susceptibility of said cells to treatment for prevention of metastasis.

2. A method in accordance with claim 1, wherein said determining step of a) comprises subjecting the tumor cells to an immunoassay using labelled antibodies against the DAP-kinase protein.

3. A method in accordance with claim 1, wherein said determining step of b) comprises:
   subjecting the DNA of the tumor cells to a treatment which converts cytosines in the DNA to uracils, except when the cytosine is methylated, and
   subjecting the converted DNA to PCR using primers directed to regions most likely to be methylated so as to distinguish between methylated and non-methylated DNA.

4. A method for treating tumor cells to decrease the chance that such cells will metastasize, comprising:
   a) screening patients for tumor cells most likely to be susceptible to treatment for prevention of metastasis in accordance with the method of claim 1; and
   b) in those patients for which said screen is positive, administering an effective amount of an agent for causing demethylation of methylated DNA, thereby decreasing the chance that such cells will metastasize.

5. A method in accordance with claim 4, wherein said agent is 5-aza-2'-deoxycytidine.

6. A method for treating tumor cells in a patient to decrease the chance that such cells will metastasize, comprising:
   determining whether DAP-kinase proteins are produced by said cells, and
   if said determining step is positive, administering to the patient an effective amount of an agent for preventing methylation of the DAP-kinase gene which produces said DAP-kinase protein, thereby decreasing the chance that such cells will metastasize.

7. A method in accordance with claim 6, wherein said agent is 5-aza-2'-deoxycytidine.

* * * * *

SEQUENCE LISTING

<160> NUMBER OF SEQ ID NOS: 4

<210> SEQ ID NO: 1
<211> LENGTH: 27
<212> TYPE: DNA
<213> ORGANISM: Homo sapiens -continued

```
<400> SEQUENCE: 1
ggaggatagt tggattgagt taatgtt                                              27

<210> SEQ ID NO: 2
<211> LENGTH: 21
<212> TYPE: DNA
<213> ORGANISM: Homo sapiens

<400> SEQUENCE: 2
caaatccctc ccaaacacca a                                                    21

<210> SEQ ID NO: 3
<211> LENGTH: 24
<212> TYPE: DNA
<213> ORGANISM: Artificial Sequence
<220> FEATURE:
<223> OTHER INFORMATION: Description of Artificial Sequence: Sense
      primer sequence for methylated gene

<400> SEQUENCE: 3
ggatagtcgg atcgagttaa cgtc                                                 24

<210> SEQ ID NO: 4
<211> LENGTH: 16
<212> TYPE: DNA
<213> ORGANISM: Artificial Sequence
<220> FEATURE:
<223> OTHER INFORMATION: Description of Artificial Sequence: Antisense
      primer sequence for methylated gene

<400> SEQUENCE: 4
ccctcccaaa cgccga                                                          16
```